United States Patent
Kane et al.

(10) Patent No.: US 8,158,009 B2
(45) Date of Patent: Apr. 17, 2012

(54) METHODS AND APPARATUS FOR FOAM CONTROL IN A VACUUM FILTRATION SYSTEM

(75) Inventors: Jeffrey F. Kane, Hudson, MA (US); Thomas Taylor, Windham, NH (US); Peter Zuk, Jr., Harvard, MA (US); Sean Landis Phillips, Lancaster, MA (US)

(73) Assignee: Roush Life Sciences, LLC, Livonia, MI (US)

( * ) Notice: Subject to any disclaimer, the term of this patent is extended or adjusted under 35 U.S.C. 154(b) by 1069 days.

(21) Appl. No.: 12/023,685

(22) Filed: Jan. 31, 2008

(65) Prior Publication Data
US 2008/0290040 A1    Nov. 27, 2008

Related U.S. Application Data

(60) Provisional application No. 60/931,445, filed on May 23, 2007, provisional application No. 60/952,010, filed on Jul. 26, 2007, provisional application No. 60/952,011, filed on Jul. 26, 2007, provisional application No. 60/952,012, filed on Jul. 26, 2007, provisional application No. 60/952,013, filed on Jul. 26, 2007.

(51) Int. Cl.
*B01D 35/00* (2006.01)
(52) U.S. Cl. ......... 210/739; 210/780; 210/406; 210/473
(58) Field of Classification Search ............ 210/808, 210/406, 739, 780, 473
See application file for complete search history.

(56) References Cited

U.S. PATENT DOCUMENTS

| | | | |
|---|---|---|---|
| 1,168,988 A | 1/1916 | Zimmermann | |
| 1,216,112 A | 2/1917 | Greven | 210/477 |
| 1,501,073 A | 7/1924 | Stead | 210/478 |
| 2,367,794 A | 1/1945 | Marselus | 210/159 |
| 2,460,423 A | 2/1949 | Kracklauer | 210/479 |
| 2,584,206 A | 2/1952 | Hodsdon | 210/445 |
| 2,608,843 A | 9/1952 | Kennedy et al. | 65/65 |
| 2,755,935 A | 7/1956 | Richards | 210/149 |
| 2,818,178 A | 12/1957 | Hodsdon | 210/445 |
| 3,010,583 A | 10/1959 | Kenyon | 210/406 |

(Continued)

FOREIGN PATENT DOCUMENTS
DE            403858        10/1924
(Continued)

OTHER PUBLICATIONS

European Patent Office, International Search Report and Written Opinion of the International Searching Authority—Application No. PCT/US2008/052642, dated Jun. 5, 2008 (16 pages).

(Continued)

*Primary Examiner* — Chester Barry
(74) *Attorney, Agent, or Firm* — Sunstein Kann Murphy & Timbers LLP

(57) ABSTRACT

A flow diverter, vacuum control and tilting of the liquid filtering system are used alternatively or in conjunction to reduce foam production in a filtered liquid sample. A liquid filtering system includes an upper sample reservoir, a filter and a lower storage bottle. A vacuum is applied below the sample filter to draw sample liquid through the sample filter into the storage bottle. A flow diverter may be used to direct flow of the filtered liquid sample onto a sidewall of the storage bottle or guide flow to a bottom of the storage bottle. The vacuum may be regulated to reduce foaming. The liquid filtering system may be tilted to direct fluid to the sidewall of the lower storage bottle and reduce foaming.

25 Claims, 15 Drawing Sheets

U.S. PATENT DOCUMENTS

| | | | | |
|---|---|---|---|---|
| 3,085,705 A | 4/1963 | Varney | | 215/41 |
| 3,286,866 A | 11/1966 | McIntosh | | 215/40 |
| 3,295,686 A | 1/1967 | Krueger | | 210/455 |
| 3,319,792 A | 5/1967 | Leder et al. | | 210/238 |
| 3,469,369 A | 9/1969 | Helmke | | 95/259 |
| 3,478,889 A | 11/1969 | Fessler | | 210/406 |
| 3,730,352 A | 5/1973 | Cohen et al. | | 210/332 |
| 3,752,651 A | 8/1973 | Bush | | 23/230 R |
| 3,838,978 A | 10/1974 | Eddleman et al. | | 23/292 |
| 3,956,125 A | 5/1976 | Strutt et al. | | 210/94 |
| 4,052,163 A | 10/1977 | Patzner | | 23/259 |
| 4,247,399 A | 1/1981 | Pitesky | | 210/341 |
| 4,251,366 A | 2/1981 | Simon et al. | | 210/767 |
| 4,301,010 A | 11/1981 | Eddleman et al. | | 210/406 |
| 4,357,240 A | 11/1982 | Mehra et al. | | 210/455 |
| 4,394,266 A | 7/1983 | Mehra et al. | | 210/244 |
| 4,468,321 A | 8/1984 | St. John | | 210/232 |
| 4,521,308 A | 6/1985 | Brimhall, Jr. et al. | | 210/330 |
| 4,523,934 A | 6/1985 | Joshua | | 55/189 |
| 4,614,585 A | 9/1986 | Mehra et al. | | 210/433.2 |
| 4,673,501 A | 6/1987 | Wells et al. | | 210/406 |
| 4,678,572 A | 7/1987 | Hehl | | 210/232 |
| 4,678,576 A | 7/1987 | Leoncavallo | | 210/433.2 |
| 4,689,147 A | 8/1987 | Leoncavallo et al. | | 210/232 |
| 4,702,834 A | 10/1987 | Relyea | | 210/321.78 |
| D297,860 S | 9/1988 | Leoncavallo et al. | | D24/8 |
| 4,783,318 A | 11/1988 | Lapakko | | 422/101 |
| 4,792,398 A | 12/1988 | Klein | | 210/406 |
| 4,832,841 A | 5/1989 | Gutman et al. | | 210/232 |
| 4,849,061 A | 7/1989 | Relyea | | 156/308.4 |
| 4,894,155 A | 1/1990 | Leoncavallo et al. | | 210/321.84 |
| 4,944,876 A | 7/1990 | Miller | | 210/321.75 |
| 5,112,484 A | 5/1992 | Zuk, Jr. | | 210/247 |
| 5,116,496 A | 5/1992 | Scott | | 210/232 |
| 5,141,639 A | 8/1992 | Kraus et al. | | 210/321.75 |
| 5,205,989 A | 4/1993 | Aysta | | 422/101 |
| 5,227,137 A | 7/1993 | Monti et al. | | 422/101 |
| 5,234,585 A | 8/1993 | Zuk, Jr. | | 210/188 |
| 5,264,184 A | 11/1993 | Aysta | | 422/101 |
| 5,283,039 A | 2/1994 | Aysta | | 422/104 |
| 5,308,483 A | 5/1994 | Sklar et al. | | 210/232 |
| 5,375,477 A | 12/1994 | Neill et al. | | 73/863.23 |
| 5,447,079 A | 9/1995 | Neill et al. | | 73/863.23 |
| 5,603,900 A | 2/1997 | Clark et al. | | 422/101 |
| 5,785,927 A | 7/1998 | Scott et al. | | 422/104 |
| 5,792,425 A | 8/1998 | Clark et al. | | 422/101 |
| 5,849,249 A | 12/1998 | Jones, Jr. et al. | | 422/101 |
| 5,873,967 A | 2/1999 | Clark et al. | | 156/70 |
| 5,948,246 A | 9/1999 | Zuk, Jr. | | 210/188 |
| 6,159,368 A | 12/2000 | Moring et al. | | 210/321.75 |
| 6,287,849 B1 | 9/2001 | McNerney et al. | | 435/287.1 |
| 6,338,802 B1 | 1/2002 | Bodner et al. | | 210/650 |
| 6,358,730 B1 | 3/2002 | Kane | | 435/297.5 |
| 6,379,625 B1 | 4/2002 | Zuk, Jr. | | 422/101 |
| 6,419,827 B1 | 7/2002 | Sandell et al. | | 210/321.75 |
| 6,443,314 B2 | 9/2002 | Shiraiwa et al. | | 210/474 |
| 6,451,261 B1 | 9/2002 | Bodner et al. | | 422/99 |
| 6,458,278 B1 | 10/2002 | Leoncavallo et al. | | 210/650 |
| 6,491,873 B2 | 12/2002 | Roberts et al. | | 422/101 |
| 6,506,343 B1 | 1/2003 | Bodner et al. | | 422/65 |
| 6,720,417 B1 | 4/2004 | Walter | | 536/25.4 |
| 6,770,203 B2 | 8/2004 | Leoncavallo et al. | | 210/650 |
| 6,783,732 B2 | 8/2004 | Madden et al. | | 422/63 |
| 6,913,152 B2 | 7/2005 | Zuk, Jr. | | 210/406 |
| 6,951,762 B2 | 10/2005 | Zuk, Jr. | | 436/180 |
| 6,986,849 B2 | 1/2006 | Irvine | | 210/791 |
| 7,011,755 B2 | 3/2006 | Zuk, Jr. | | 210/416.1 |
| 2002/0096468 A1 | 7/2002 | Zuk, Jr. | | 210/455 |
| 2002/0098125 A1 | 7/2002 | Roberts et al. | | 422/101 |
| 2003/0010708 A1 | 1/2003 | Leocavallo et al. | | 210/477 |
| 2003/0080045 A1 | 5/2003 | Zuk, Jr. | | 210/416.1 |
| 2005/0023172 A1 | 2/2005 | Ide et al. | | 206/446 |
| 2005/0178216 A1 | 8/2005 | Pitt et al. | | 73/863.23 |
| 2007/0144959 A1 | 6/2007 | Zuk, Jr. | | 210/473 |

FOREIGN PATENT DOCUMENTS

| | | |
|---|---|---|
| DE | 33 06 599 | 8/1984 |
| EP | 0 075 687 | 4/1983 |
| EP | 0 857 961 A2 | 8/1988 |
| EP | 0 223 323 | 5/1990 |
| EP | 0 618 833 | 12/1992 |
| EP | 1 031 371 | 8/2000 |
| EP | 1 145 752 | 10/2001 |
| GB | 2 250 927 | 6/1992 |
| WO | WO 93/12853 | 7/1993 |
| WO | WO 95/04585 | 2/1995 |
| WO | WO 98/32875 | 7/1998 |
| WO | WO 2007/028157 | 3/2007 |

OTHER PUBLICATIONS

The International Bureau of WIPO, International Preliminary Report on Patentability—Application No. PCT/US2008/052642, dated Nov. 24, 2009 (10 pages).

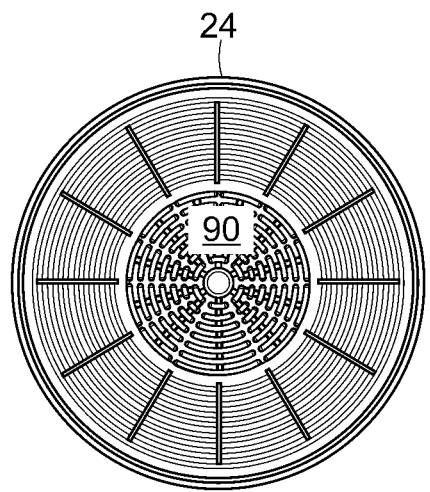
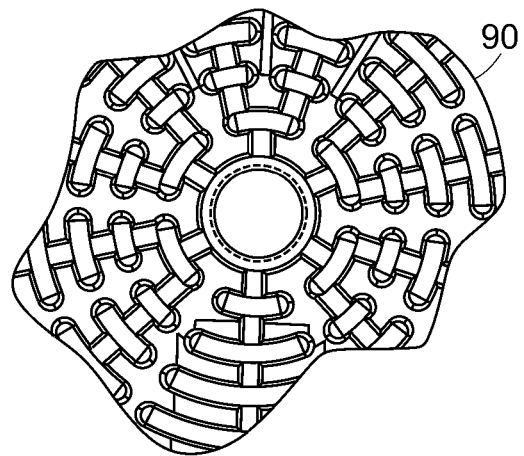
FIG. 3a  FIG. 3b
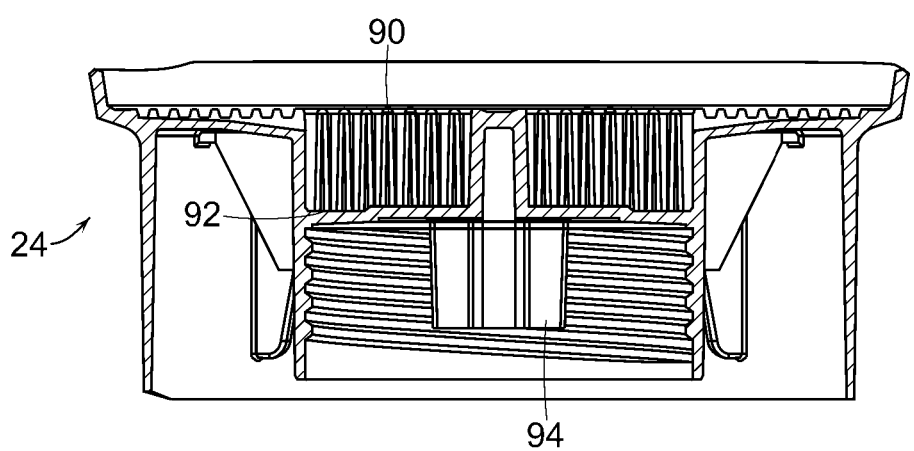
FIG. 3c

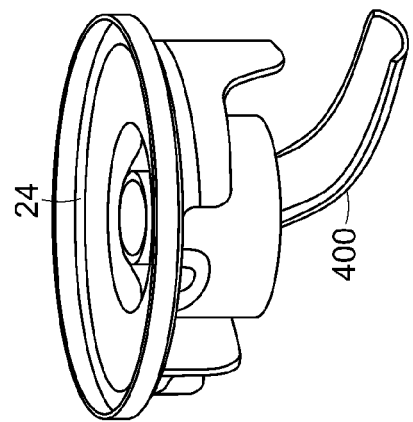
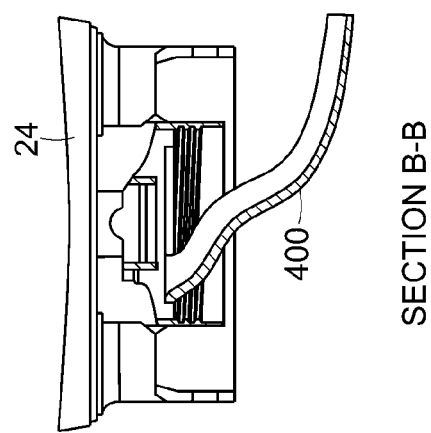
SECTION B-B
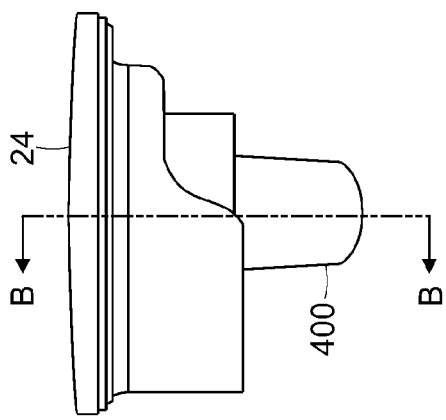
FIG. 7

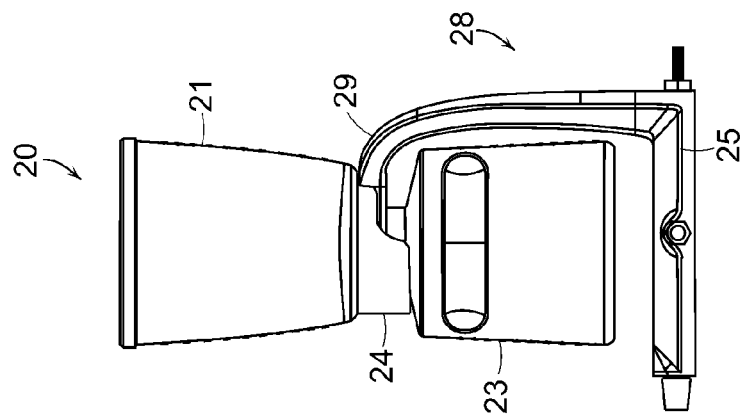
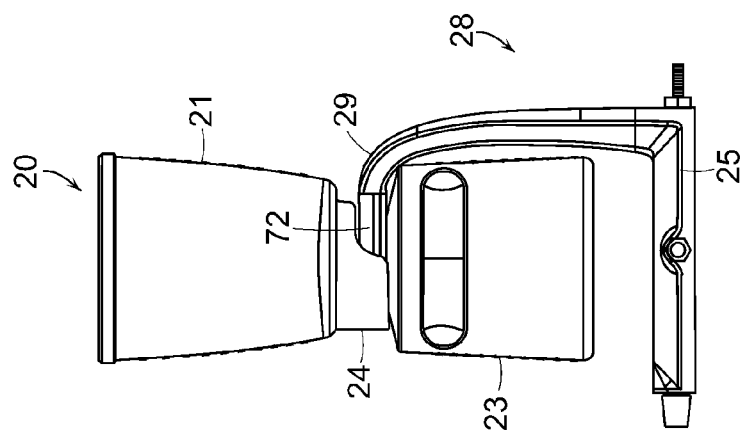
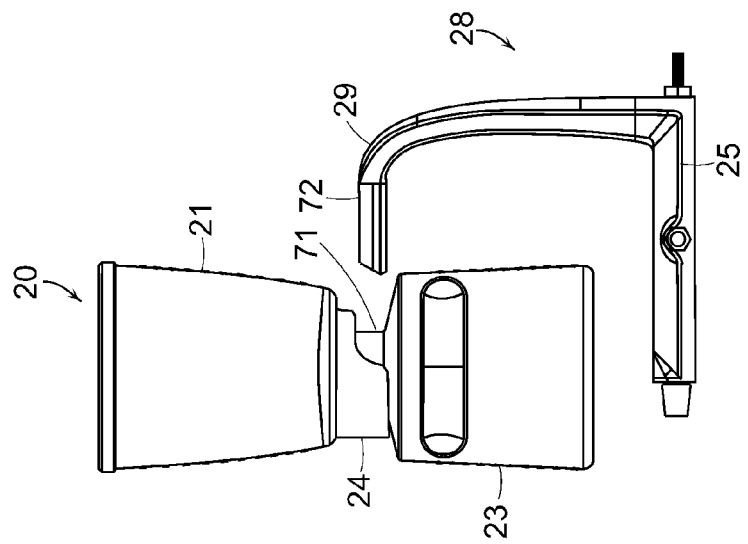
FIG. 13c
FIG. 13b
FIG. 13a

METHODS AND APPARATUS FOR FOAM CONTROL IN A VACUUM FILTRATION SYSTEM

The present application claims priority from U.S. Provisional Application No 60/931,445, filed May 23, 2007, entitled "Vacuum Filtration Device and Method," the full disclosure of which is hereby incorporated by reference herein. The present application further claims priority from U.S. Provisional Application No. 60/952,010, entitled "Vacuum Bottle", No. 60/952,011, entitled "Vacuum Base," No. 60/952,012, entitled "Vacuum Collar," and No. 60/952,013, entitled "Vacuum Controller," all of which were filed Jul. 26, 2007 and the full disclosures of which are hereby incorporated by reference herein. The present application is related to applications with the following titles and attorney docket numbers: "Vacuum Base and Related Methods and Apparatus for Vacuum Filtration," Ser. No. 12/023,711; "Method and Apparatus for Filtrate Storage Handling," Ser. No. 12/023,757; "Methods and Apparatus for Supporting a Vacuum Filtration Device," Ser. No. 12/023,820 all filed on the same date herewith, the full disclosures of which are hereby incorporated by reference herein.

FIELD OF THE INVENTION

The present invention relates to liquid filtration, and particularly to a vacuum bottle for a vacuum filtration system for filtering liquid samples.

BACKGROUND ART

Entities such as pharmaceutical companies and university research labs commonly use vacuum filtration sterilization of biological fluids such as cell culture media and buffer solutions. This typically involves what are referred to as bottle-top filters such as the three-piece example shown in FIG. 1. A bottle-top filter device 10 includes an upper unfiltered sample reservoir 11 which is removable and disposable. The sample reservoir 11 includes a filter 12 which typically includes a polyethersulfone (PES) or cellulose-based membrane for sterilized filtering of the sample liquid. The upper rim of the sample reservoir 11 may receive a removable cover that protects the sample liquid from contamination. On the bottom is a filtrate storage bottle 13 for collecting the liquid filtrate, and in between is a vacuum collar 14 with a vacuum port for manual coupling of a vacuum source. Vacuum is applied downstream of the filter 12 to create a pressure differential which draws the sample liquid through the filter into the storage bottle 13. The upper rim of the storage bottle 13 may be adapted to receive a cap to close the container after filtering once it is disconnected from the vacuum collar 14. These components are normally sold pre-sterilized.

Such products and processes have various inherent challenges. For example potential spills are a significant concern. A spill can disrupt production for up to an entire day and require use of a sanitizing laminar hood. Moreover, the bottle-top filter device 10 of FIG. 1 is top heavy, especially when first filled with sample liquid, making the device unstable and prone to tipping. The need for manual attachment of the vacuum source to the vacuum port of the vacuum collar 14 creates further problems with instability. These issues can lead to greater risk of spillage, increased setup time, and a need for full-time supervision.

When vacuum filtration systems are used with cell culture media and the like, another concern is foaming. Filtrate pulled through the filter is apt to fall into the storage bottle and splash. Splashing can cause foaming of the filtered sample. Foam can damage cells and/or proteins, making it undesirable for filtered cell culture media to contain foam.

SUMMARY OF THE INVENTION

A liquid filtering assembly has an upper sample reservoir for receiving a volume of sample liquid. A sample filter is positioned proximate a bottom of the sample reservoir for mechanically filtering the sample liquid. A lower storage bottle receives filtered sample liquid from the sample reservoir. A vacuum in fluid communication with the lower storage bottle serves to draw sample liquid through the sample filter into the storage bottle. A flow diverter is positioned to receive sample liquid drawn through the sample filter and to direct the sample liquid onto a sidewall of the lower storage bottle. Flow along the sidewall advantageously reduces splashing and foaming.

The flow diverter may include a bendable neck element. A vacuum collar may be disposed between the upper sample reservoir and the lower storage bottle. In alternative embodiments, the flow diverter is constructed integral with the vacuum collar. In a further alternate embodiment, the flow diverter is integral with the lower storage bottle. In a still further embodiment, the flow diverter is a tube connected to receive the filtered sample liquid and guide it down close to the bottom of the storage bottle.

A base receives an inserted filter assembly to hold the assembly securely above a work surface. The base may include a weighted bottom to avoid tipping over. The base can be advantageously designed to couple a vacuum to the vacuum collar. A fluid conduit through the base connects a vacuum inlet port with a vacuum outlet port. The vacuum outlet port is arranged in a cradle for connection to the liquid filter assembly. The cradle is on a support arm secured to the weighted bottom of the base. The cradle is movable relative to the weighted bottom so as to adjustably hold the liquid filter assembly at a tilted non-vertical angle. Adjustment may be provided by flexibility of the support arm in one embodiment. Alternatively, the cradle may be pivotable with respect to the support arm. The tilted assembly can urge flow of filtrate along the sidewall to reduce splashing and foaming.

Splashing and foaming can be further avoided by controlling the pressure level of the vacuum. For this purpose, it is advantageous to provide a vacuum controller accessible atop the work surface to regulate the vacuum. In a specific embodiment, the base couples the vacuum to the liquid filter assembly and a vacuum controller is provided on the base to regulate fluid flow through a fluid conduit that connects a vacuum inlet port on the base to a vacuum outlet port. The vacuum outlet port may be arranged in a cradle for connection to the liquid filter assembly. The vacuum controller may include a knob having an off position for venting the fluid conduit to the atmosphere so that no vacuum pressure is provided to the lower storage bottle.

Methods of the present invention for filtering liquid samples involve securing a filter assembly above a work surface. The filter assembly includes an upper reservoir above a filter and a storage bottle below the filter for receiving filtered liquid drawn through the filter. A liquid sample is deposited in the upper reservoir and a vacuum applied underneath the filter to draw liquid through the filter. A vacuum controller is adjusted to regulate the applied vacuum so as to reduce foaming of the filtered liquid sample. Other actions that may be taken include tilting the filter assembly to cause the filtered liquid to flow along a sidewall of the storage bottle. Alternatively, flow of liquid may be directed along a diverter onto the sidewall of the storage bottle or guided through a tube to the bottom of the storage bottle.

Other objects and advantages of the present invention will become apparent during the following description of specific embodiments of the invention, taken in conjunction with the drawings.

BRIEF DESCRIPTION OF THE DRAWINGS

FIG. 3a is a plan view of a vacuum collar.

FIG. 3b is a magnified section of the vacuum collar of FIG. 3a.

FIG. 3c is a side cross-sectional view of the vacuum collar of FIG. 3a.

FIG. 3d is a side cross-sectional view taken through the vacuum port on the vacuum collar of FIG. 3a.

FIG. 7 shows an example of a flow diverter which is integral with the vacuum collar.

FIGS. 13A-C illustrate docking of a liquid filter assembly onto a base.

FIGS. 14A and 11B illustrate registration of the vacuum collar with the cradle.

DETAILED DESCRIPTION OF SPECIFIC EMBODIMENTS

Figure 1:
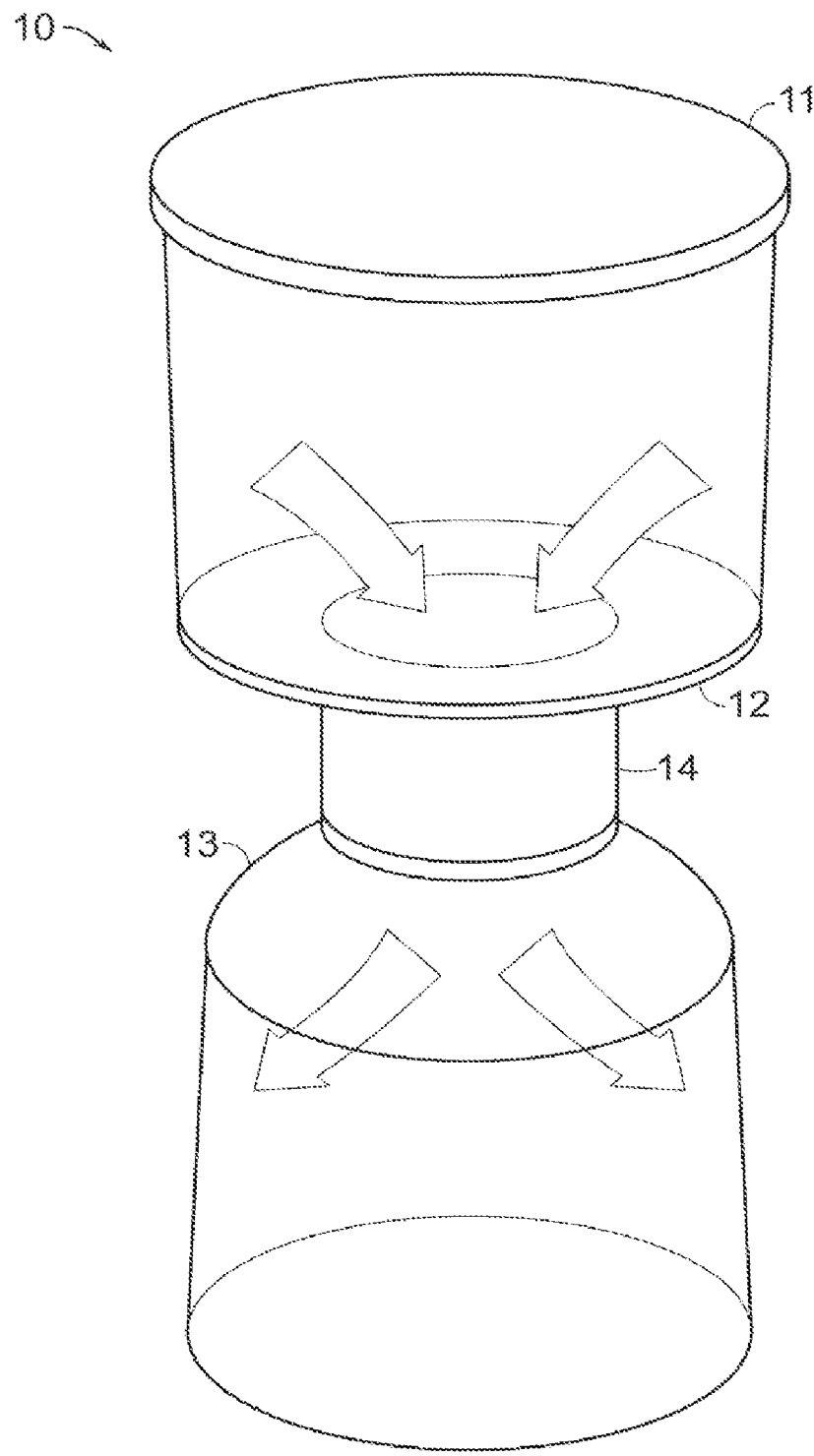
FIG. 1 shows an example of a bottle-top filter device according to the prior art.
Figure 2:
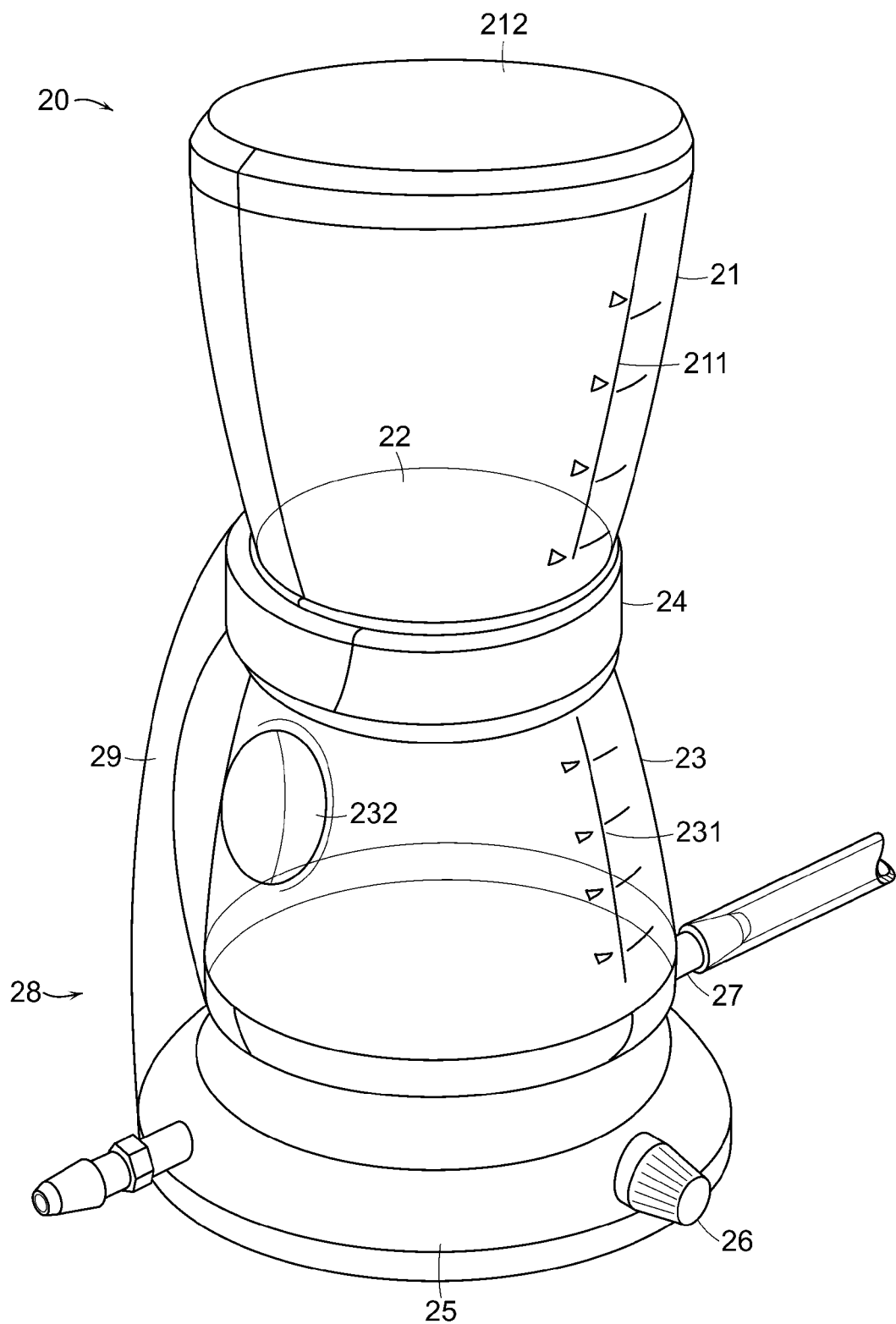
FIG. 2 shows an embodiment of a liquid filtration system according to the present invention.
Figure 3D:
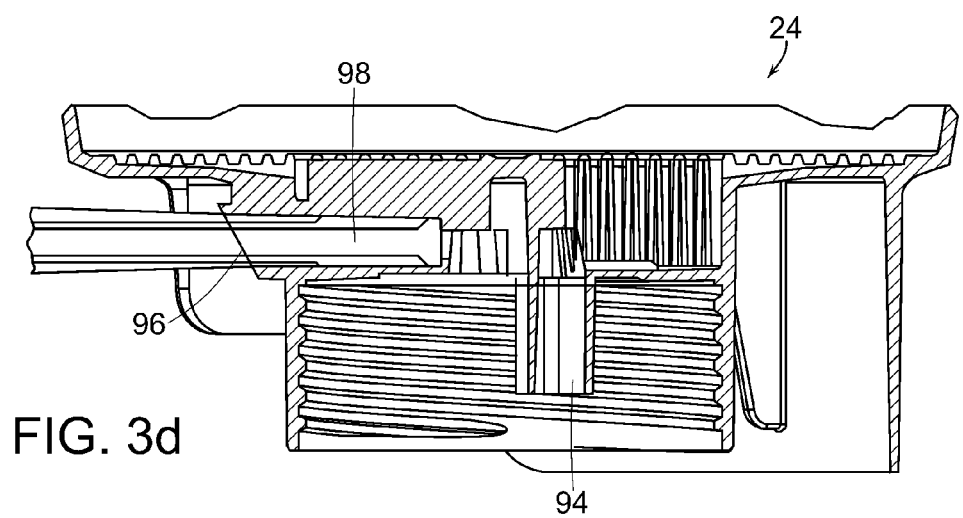

Referring now to FIG. 2, a liquid filtration system 20 includes a vacuum bottle 23. The vacuum bottle 23 is connected by a vacuum collar 24 to an upper sample reservoir 21, which together form a unified filter assembly. The filter assembly is preferably disposable and pre-sterilized. The vacuum bottle 23 may have male threads around its top opening, which screw into female threads of the vacuum collar 24. Any other type of releasable attachment between the vacuum bottle 23 and the vacuum collar 24 could be used, such as, for example, press fit. The vacuum collar 24 likewise attaches to the bottom of the upper sample reservoir 21. Alternatively, the vacuum collar 24 may be integral with the upper sample reservoir 21. The vacuum collar 24 itself is preferably a one piece molded element, but may be made as a plurality of elements such as a top funnel portion and a bottom threaded member with a vacuum port. Possible materials for the vacuum collar include but are not limited to, acrylic, polycarbonate, styrene, polyethylene, and polypropylene.

The sample reservoir 21 receives a volume of unfiltered sample liquid and has at its inner bottom a sample filter 22 for mechanically filtering the sample liquid. The filter may be a microporous filter element, or a depth filter element, and may be either hydrophilic or hydrophobic depending on the type of liquid being filtered. Representative filter materials include cellulose nitrate, cellulose acetate, mix esters of cellulose, Teflon®, PVDF, nylon, polypropylene, polyethylene, polycarbonate and glass fibers, but are not limited to these materials. The vacuum collar 24 is disposed between the sample reservoir 21 and the storage bottle 23 for applying a vacuum to an underside of the sample filter 22 which draws sample liquid through the sample filter into the storage bottle. The vacuum collar 24 provides a flat top plane on which the filter is supported. The filter 22 may be sealed to the top plane of the collar to prevent any unfiltered liquid from entering the storage bottle 23. In particular, the filter may be sealed about its outer periphery. The seal could be a heat seal, an ultrasonic seal, a solvent seal, a glue seal, an RF seal, or a seal ring seal, or any other type of seal that prevents the flow of unfiltered liquid into the outlet chute 94. The flat top plane must nevertheless have openings through which the filtered liquid is pulled.

As shown in FIGS. 3a-3d, one structure for providing the openings and the support is a maze of vanes 90. The top edges of the vanes 90 support the filter and the liquid may be pulled down between the vanes. A solid bottom layer 92 covers a substantial portion of the maze of vanes 90. An open outlet chute 94 provides the only fluid communication between the sample reservoir 21 and the vacuum bottle 23. Thus, filtered fluid from the downstream surface of the filter is channeled through the vanes 90 into the outlet chute 94. An assembly vacuum port 96 is provided out the side of the vacuum collar 24 for connection with a source vacuum. A passage 98 from the assembly vacuum port 96 connects the vacuum to a volume below the solid bottom layer of the collar. The vacuum is directed into the vacuum storage bottle 23 for pulling liquid through the outlet chute 94 into the vacuum bottle. The vacuum storage bottle 23, thus, receives filtered sample liquid from the sample reservoir 21.

The filter assembly is secured to a base 28. The base 28 includes a weighted bottom 25 to prevent the liquid filtration system from tipping over and to provide a stable support to the filter assembly which minimizes the potential for spills and accidents. The base 28 receives an inserted filter assembly and secures it in a stable position.

Figure 14A:
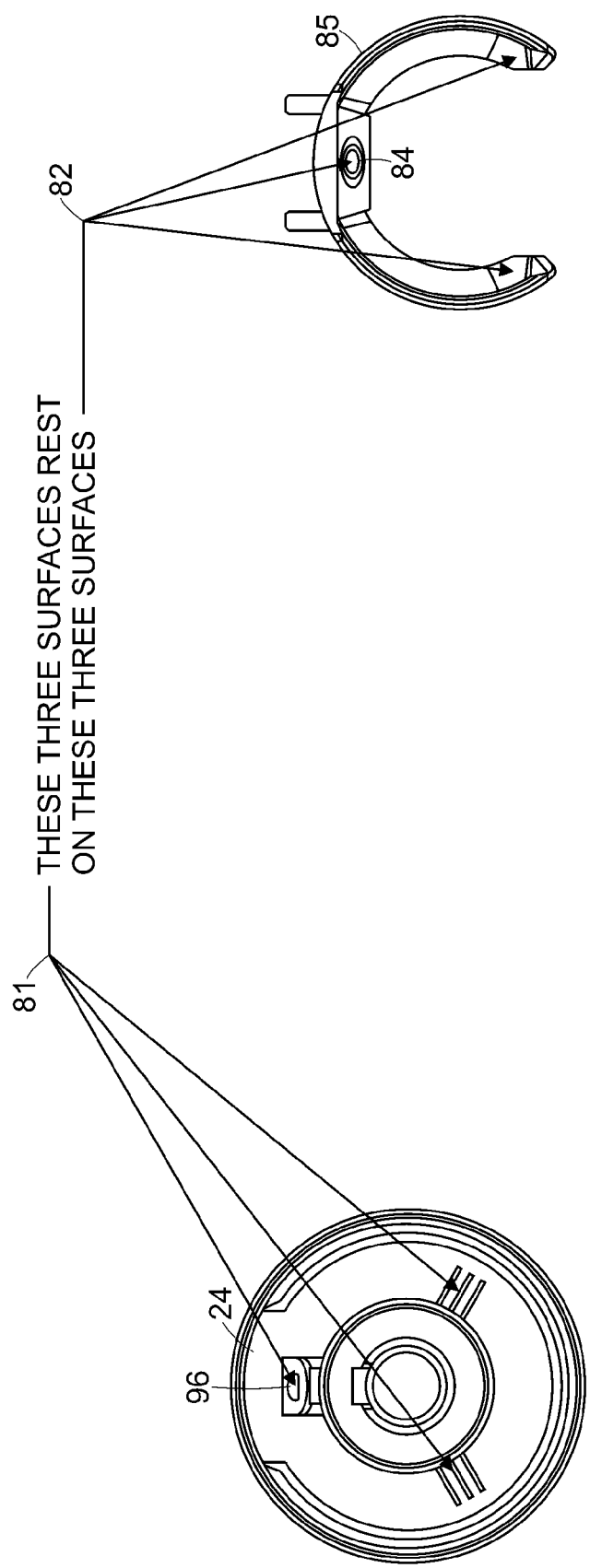
Figure 14B:
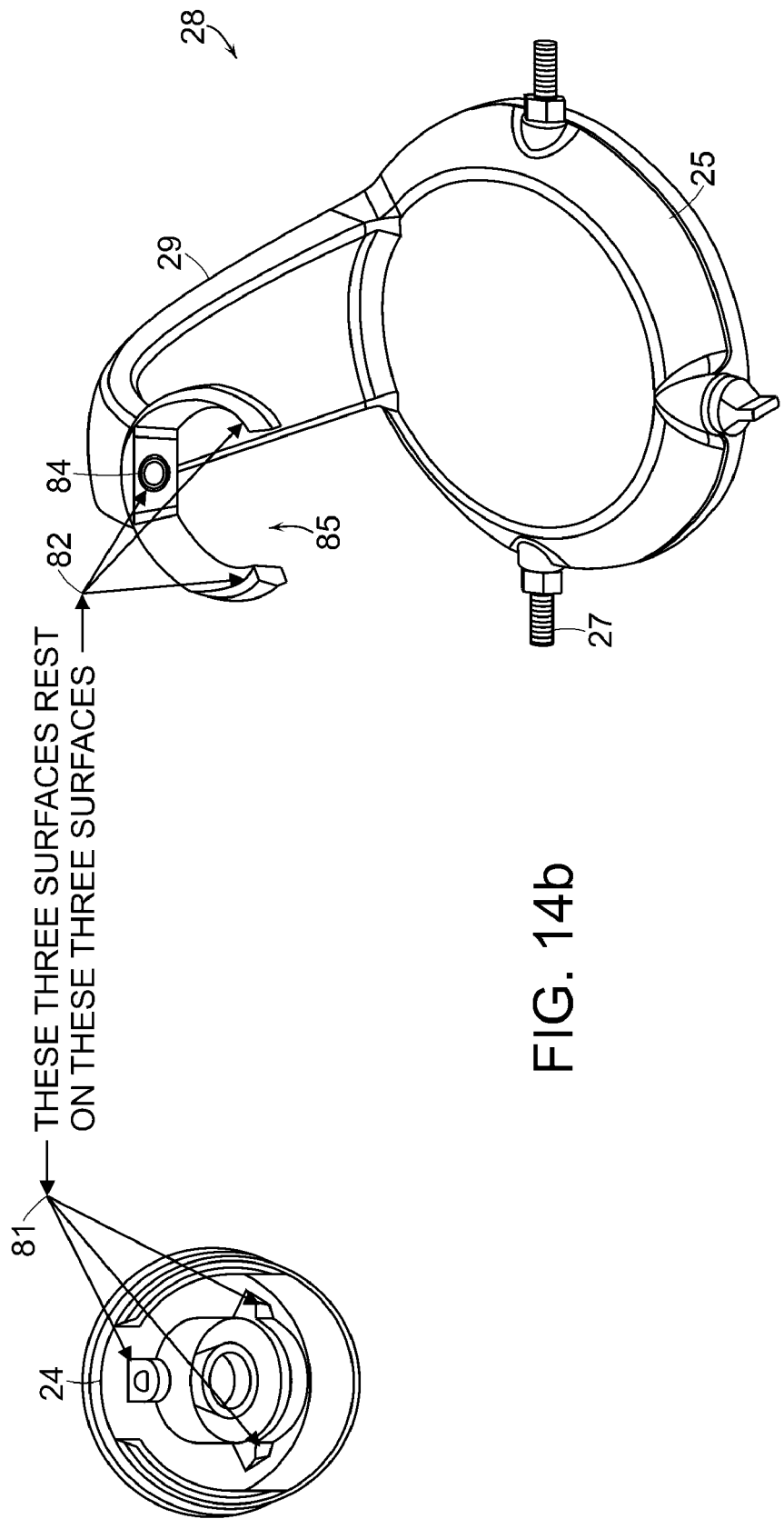

The base 28 also couples the vacuum to the vacuum collar 24, as illustrated in FIG. 14. A source vacuum is provided to the base through a vacuum inlet port 27. Within the base, a fluid conduit provides a path for the vacuum that extends up through the support arm 29 to a vacuum outlet port 84 in a cradle 85 for mating with the vacuum collar 24.

The filtration apparatus functions as follows. The lid on the upper sample reservoir is removed to allow a quantity of unfiltered liquid to be poured into the reservoir. Air is pulled out of the storage bottle 23 through the vacuum ports to the source vacuum. The top surface of the unfiltered liquid in the upper sample reservoir 21 will be kept at atmospheric pressure by the open top of the reservoir or, if the lid is replaced, by a vent in the lid. Therefore, a differential pressure will exist between the positive pressure of the liquid on the upstream side of the filter and the negative pressure on the downstream side of the filter. The liquid will pass down through the filter. The filtered liquid will be channeled through the vanes 90 into the outlet chute 94. If no accommodations are made, the filtered fluid may drop into the storage bottle 23 and splash upon hitting the fluid already collected in the bottle. Such splashing may cause undesirable foaming.

Splashing within the storage bottle 23 and thus foaming can be minimized by adjusting the vacuum so as not to draw the fluid too vigorously down into the storage bottle 23. Higher velocity fluid flow landing on the surface of filtered liquid collected in the storage bottle 23 contributes to excessive foaming. Such high velocity flow can cause splashing that leads to foam creation. A vacuum controller 26 is included in an embodiment of the invention to allow a user to reduce the vacuum to reduce or eliminate foaming due to an overly vigorous flow. The controller regulates the vacuum to the vacuum collar 24 to precisely control pressure within the storage bottle 23. The vacuum controller 26 has a detented OFF position when it is turned fully counter-clockwise, which vents the system to atmosphere or otherwise shuts off the vacuum so that no vacuum pressure is applied to the vacuum collar 24. An initial low vacuum ON position is created by turning the vacuum controller 26 from the OFF detent clockwise about 5-15° to start applying a low vacuum to the vacuum collar 24 and create a small amount of negative pressure in the storage bottle 23. This creates an initial pressure differential across the sample filter 22 to start pulling sample liquid through the filter into the sample bottle. Continuing to turn the vacuum controller 26 further clockwise increases the vacuum to the vacuum collar 24 until some maximum source vacuum is reached when turned a full 180° clockwise. The vacuum controller 26 can work with as little as 5" Hg source vacuum up to maximum vacuum (i.e. 29.9" Hg). Any negative pressure beneath the sample filter will accelerate fluid flow down through the filter. Mechanisms for vacuum control are well known in the art. Any such controllers including diaphragm vacuum regulators, needle valve meters or other vacuum regulators may be used within the scope of the present invention.

Figure 12:
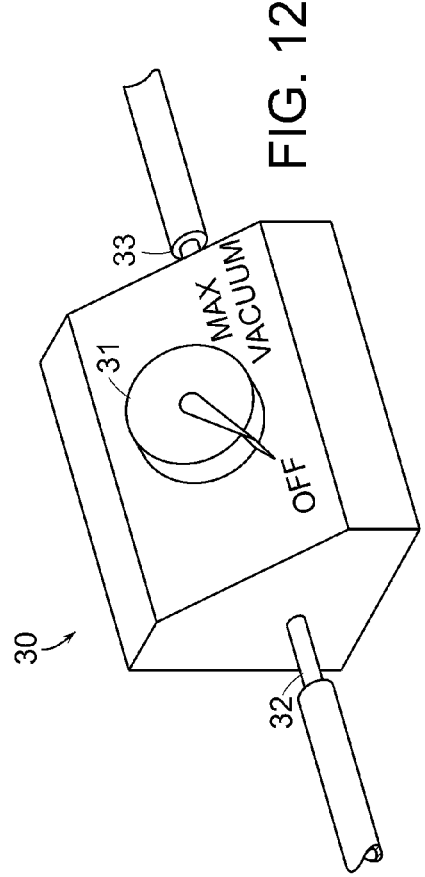
FIG. 12 shows an example of an in-line vacuum controller according to one embodiment of the present invention.

In addition or alternatively, as shown in FIG. 12, an embodiment may be based on a vacuum controller 30 which is physically separate from the base 28. Such a vacuum controller would be made accessible atop the work surface on which the base 28 sits. For most convenience, the vacuum controller would be within arms reach for a technician standing in front of the filtration system. The vacuum controller 30 includes a system vacuum inlet port 32 and a controlled vacuum outlet port 33 which provides controlled and regulated vacuum pressure to the vacuum inlet port 27 of the base 28. A vacuum control knob 31 allows for control of the regulated vacuum pressure passed through to the vacuum outlet port 33.

As with the onboard controller, the vacuum control knob on the separate vacuum controller 30 may have a detented OFF position, e.g. fully counter-clockwise, which vents the system to atmosphere or otherwise shuts off the vacuum so that no vacuum pressure is provided to the vacuum outlet port 33. An initial low vacuum ON position is created by turning the vacuum control knob 31 from the OFF detent clockwise about 5-15° to start applying a low vacuum out of the vacuum outlet port 33. Continuing to turn the vacuum control knob 33 further clockwise increases the amount of vacuum provided by the vacuum outlet port 33 until a maximum source vacuum is reached when turned a full 180° clockwise. The vacuum controller 30 can work with as little as 5" Hg source vacuum up to maximum vacuum (i.e. 29.9" Hg).

Figure 15:
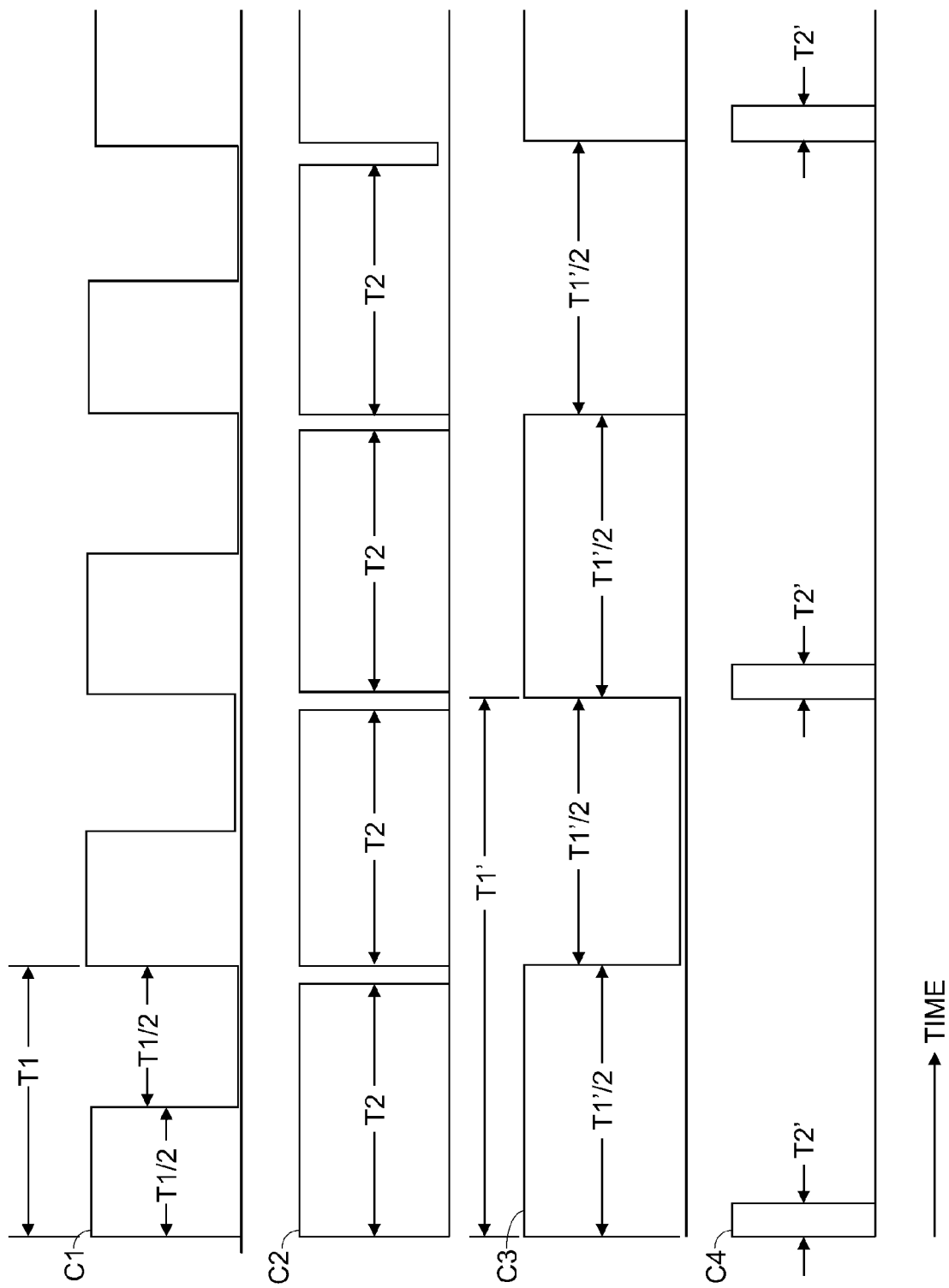
FIG. 15 is a timing diagram of a vacuum control apparatus.

The vacuum controller, whether onboard or inline, can be accomplished by a two way vacuum valve that can turn on and off the vacuum to the storage bottle. Referring to FIG. 15, curve C1 shows the output of an astable (free-running) multivibrator. Curve C2 shows the output of a monostabele (one shot) multivibrator that is triggered by the rising or leading edge of the astable multivibrator shown by curve C1. The time interval of monostable multivibrator C2 is adjusted so that its on time T2 is close to time T1, the time interval of one complete cycle of the astable multivibrator. If the output of the monostable multivibrator is used to turn on the two way vacuum valve, close to full vacuum will be applied to the vacuum inlet of the disposable vacuum filtration device. If on the other hand the astable multivibrator is adjusted to have a complete cycle time interval T1' as shown by curve C3, and the monostable multivibrator is adjusted to have an on time of T2' as shown by curve C4, then the two way vacuum valve will be turned on for short intervals of time followed by long off times, thereby applying a low average value of vacuum to the vacuum inlet of the disposable vacuum filtration device, therefore reducing the flow rate of filtered liquid entering the receptacle in any of the embodiments of the disposable vacuum filtration device of the present invention. Although the vacuum control is described using astable and monstable multivibrators, any type of control circuit that varies the on time of the vacuum valve control pulses and the time interval between them may be used.

Referring now to the liquid filter assembly, the sample reservoir 21 is an easy to use design that cooperates with the other elements of the system for an easy drop-in to the base 28 that is intuitive and requires no additional step to dock into place. The front of the sample reservoir 21 has accurate, easy to read graduation marks 211 that face the front when the filter assembly is docked in the base 28 for easy and reliable measurements. The sample filter 22 at the bottom of the sample reservoir 21 covers the filter support, whether it be the maze of vanes or other construction. On top of the sample reservoir 21 is a removable reservoir cap 212. Liquid to be filtered can be added with the reservoir cap 212 removed. The bottom of the sample reservoir 21 is adapted (e.g., threaded) for easy connect and disconnect to the vacuum collar 24.

Figure 10:
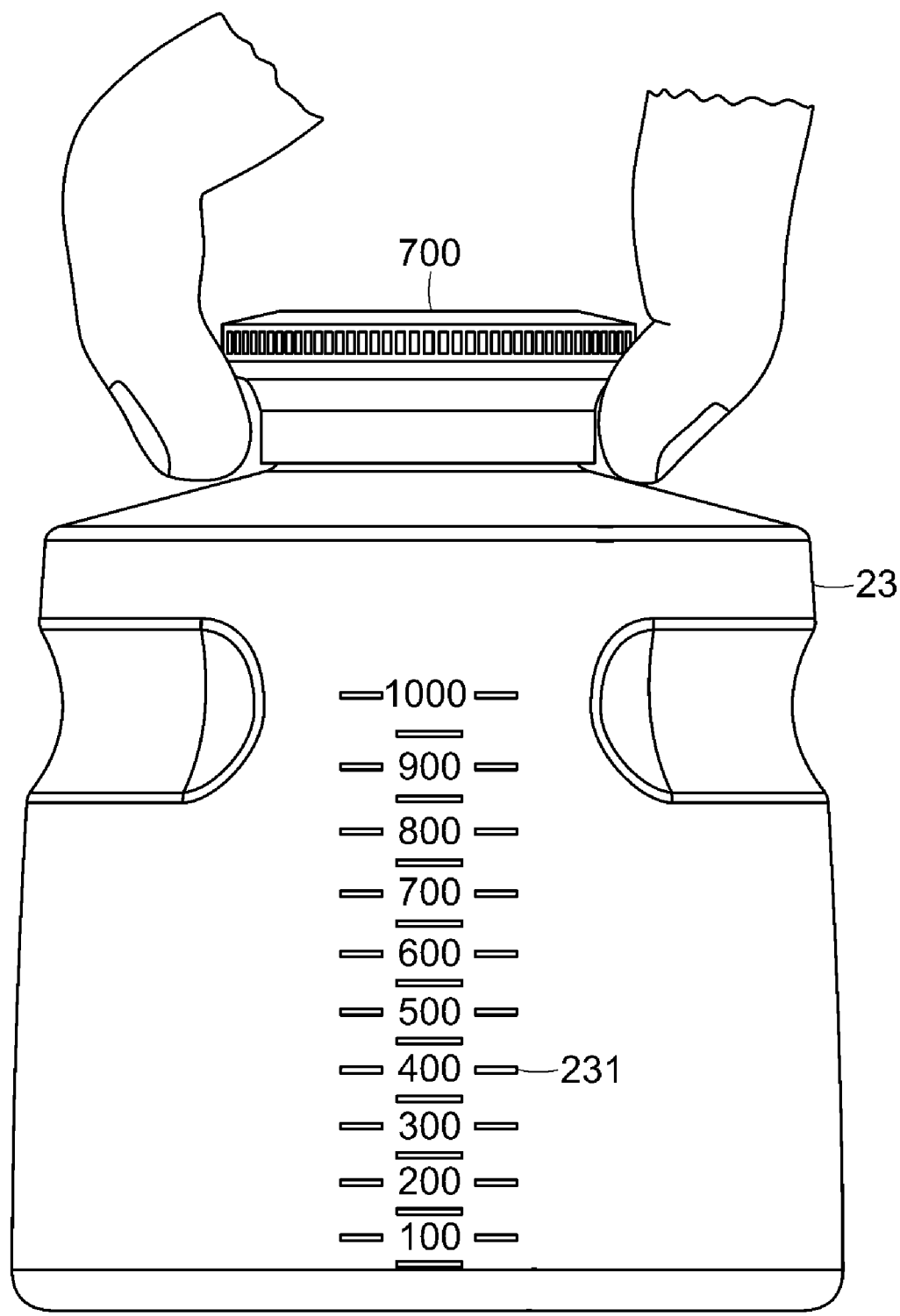
FIG. 10 shows a bottle storage cap.

The storage bottle 23 has similar features to minimize spills and accidents. The sides of the storage bottle may include opposing flat gripping surfaces 232 for secure handling. After filtering a sample, the storage bottle 23 may be disconnected from the vacuum collar 24. As shown in FIG. 10, the storage bottle 23 may be covered with a bottle cap 700, which has a radially outward protruding lip that allows for easy vertical pick-up, for example, for when the storage bottle 23 is in a water bath. The top surface of the bottle cap 700 is flat and easy to use for writing and labeling. The storage bottle 23 may come in various different sizes, e.g., 250 ml, 500 ml, 1000 ml. The front of the storage bottle 23 has accurate, easy to read graduation marks 231 that face the front when the filter assembly is docked in the base 28 for easy and reliable measurements. The top of the storage bottle 23 is adapted (e.g., threaded) for easy connect and disconnect to the vacuum collar 24.

Figure 4:
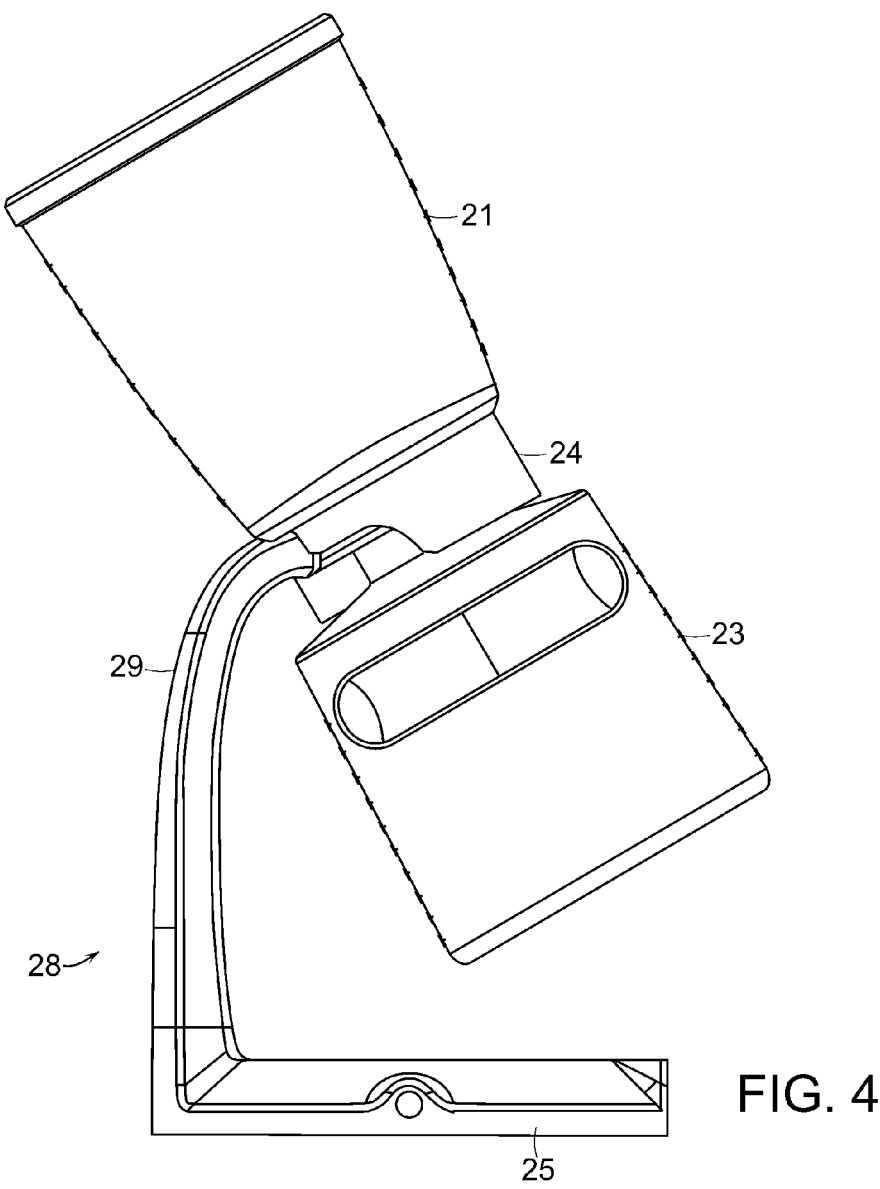
FIG. 4 shows an embodiment of the present invention in which the system components are adapted to operate at a non-vertical angle in order to help minimize foaming of the filtered sample liquid.

In addition to or alternatively to vacuum regulation, foaming can be reduced by causing liquid drawn through the filter to flow along a sidewall of the storage bottle 23. This can be accomplished by tilting the liquid filtration assembly to a non-vertical angle during the filtering process. By flowing along the sidewall the liquid is less likely to splash as compared with falling vertically down into a pool of collected liquid sample. When liquid is directed onto the sidewall, the liquid may adhere to the sidewall and flow into the collected pool of liquid in a non-turbulent manner. As shown in FIG. 4, the system components may be adapted to operate at a non-vertical angle. Flexibility may be provided in the support arm 29 to permit adjustment of the angle of the liquid filter assembly. Bending of the support arm 29 may accomplish moving the cradle 85 to a new angular position. In the alternative, the cradle 85 may be pivotable with respect to the support arm to adjust the angle of the liquid filter assembly. For example, the cradle 85 may attach to the support arm 29 by means of a universal joint.

Further embodiments may include a flow diverter for directing liquid flow onto an inner surface of the storage bottle 23, either a sidewall or the bottom of the bottle. This provides another alternative method for minimizing foaming as the filtered sample liquid enters the storage bottle 23. The liquid may be directed onto the sidewall at any height from the top of the bottle down to the bottom, depending on the design of the bottle. Preferably, the sidewall will act as a conduit for the liquid so as to avoid substantial free falling of liquid into the pool of collected liquid with associated violent splashing. Guiding the liquid in a tube to the bottom of the storage bottle is alternative arrangement that completely eliminates free fall of liquid. The flow diverter may be a fixed and/or a bendable neck element.

Figure 5:
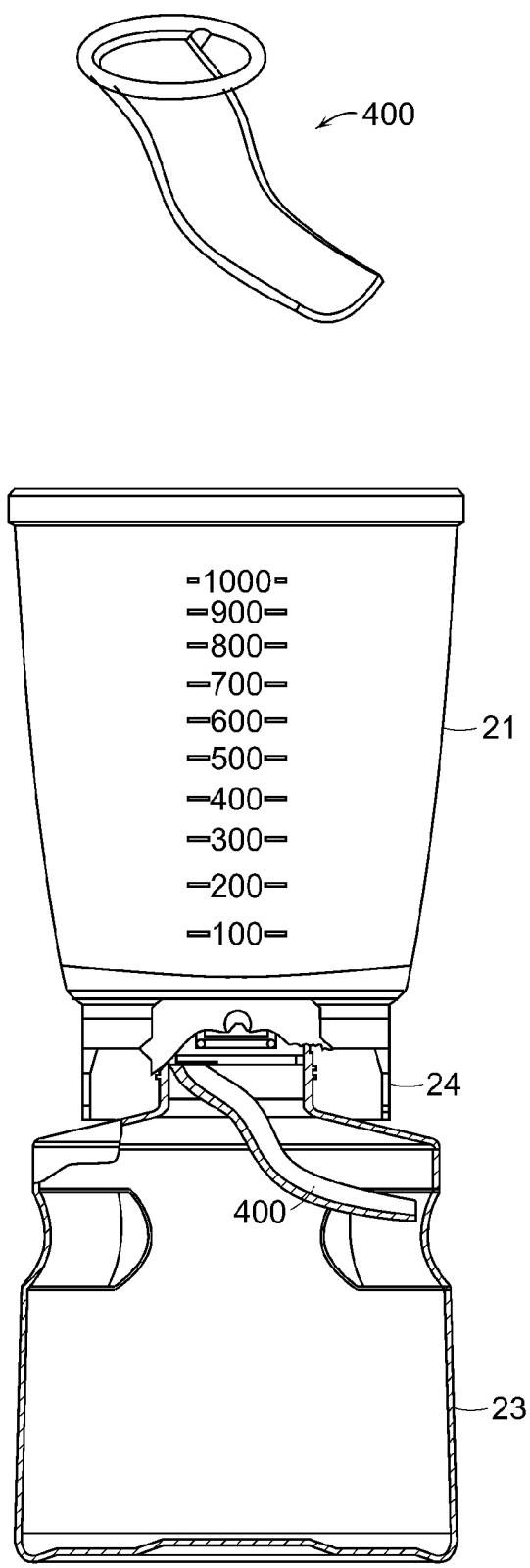
FIG. 5 shows details of a liquid filtration system flow diverter according to one embodiment of the present invention.
Figure 6:
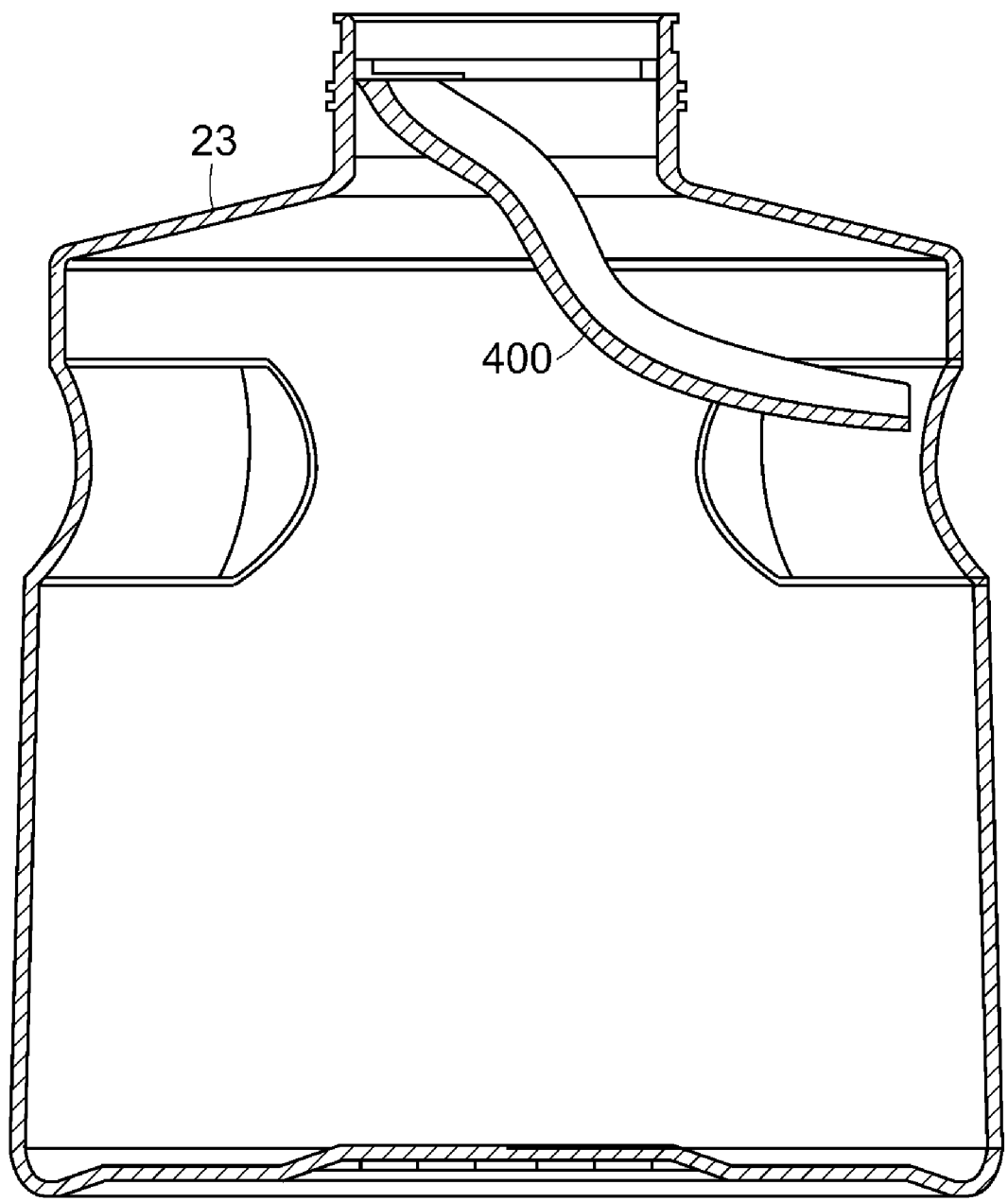
FIG. 6 shows as example of a flow diverter which is integral with the storage bottle.

FIG. 5 shows one specific embodiment of a flow diverter which utilizes a filtrate trough 400 which minimizes foaming of the filtered sample liquid by directing its incoming flow against the sidewall of the storage bottle 23. The flow diverter 400 may be a separate component added into the system to reduce foaming. Alternatively, the flow diverter 400 may be integral with the storage bottle 23 as shown in FIG. 6 or it may be integral with the vacuum collar 24 as shown in FIG. 7.

Figure 8:
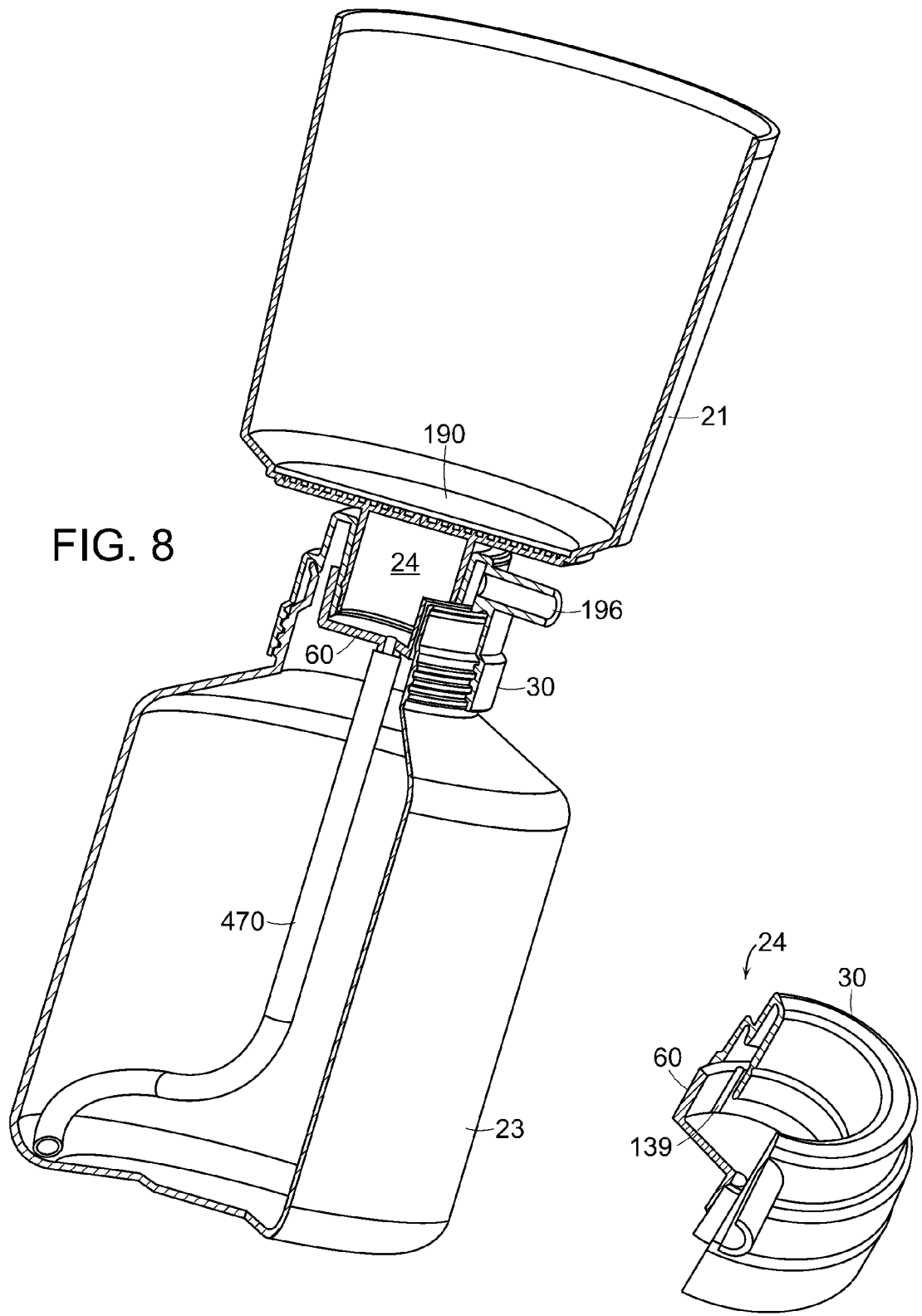
FIG. 8 shows an alternate liquid filter assembly with a flow diverter tube.
Figure 9:
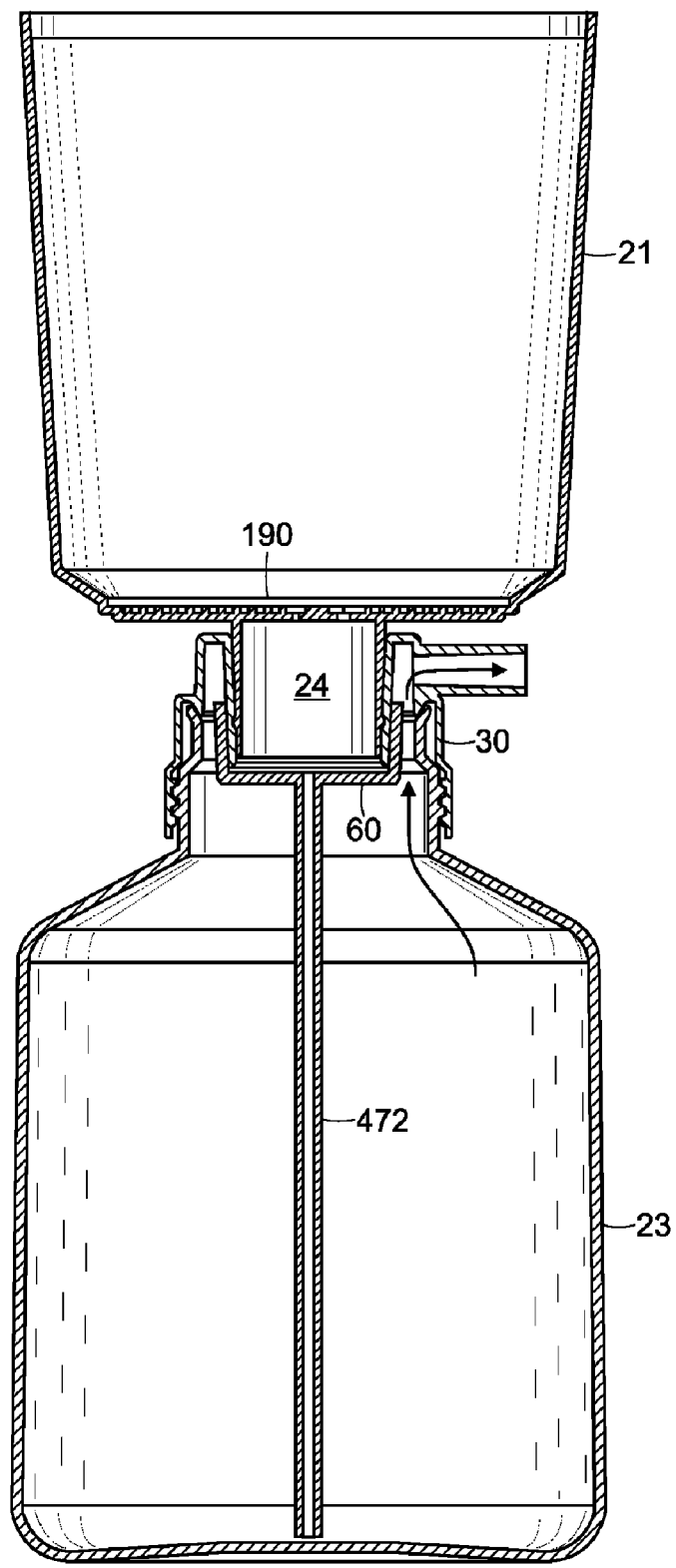
FIG. 9 shows a further alternate liquid filter assembly with a flow diverter tube.

FIGS. 8 and 9 show embodiments in which the flow diverter minimizes foaming of the filtered sample liquid by directing its incoming flow onto the bottom of the storage bottle 23. Here, the flow diverter is a tube 470 providing a passage from the vacuum collar 24 down to the bottom of the storage bottle. Liquid enters beneath the accumulating liquid in the bottle instead of splashing onto the surface of the rising supply of filtered liquid. The storage bottle is thus filled from the bottom up. If the area of the inside cross-section of the flow diverter tube 470 is made sufficiently small the flow rate of filtered liquid flowing through the tube will be reduced for a given value of negative pressure created by the vacuum source, thereby further minimizing the formation of foam on the surface of the filtered liquid.

The flow diverter tube 470 also prevents filtered liquid from entering into the assembly vacuum port 196 in the assembly of FIG. 8. The seal between the outer periphery of filter 190 and top plane of the collar prevents unfiltered liquid from passing into the storage bottle 23. If the bubble point of filter 190 for the liquid being filtered is greater than the differential pressure across the filter element when the filtration process is complete (i.e. the value of the negative pressure created by the vacuum source because the pressure on the upstream surface of the filter will be atmospheric), the pores of the filter will remain wetted, and flow through the filter will stop once all of the liquid level in the funnel reaches the upstream surface of the filter. The operator will then turn off the vacuum source and vent the inside of the storage bottle 23. If the bubble point of the filter is greater than the value of the vacuum that was applied during filtration, and if the inside cross-sectional area of tube 470 is sufficiently small, the volume between the outlet chute and the filter will retain a vacuum, and any filtered liquid in the tube 470 or the volume beneath the filter will remain there after the vacuum collar 24 and reservoir 21 are removed from the storage bottle 23.

Referring to FIG. 8a, if groove 139 is added between an adapter portion 30 of the vacuum collar and a collector portion 60 of the collar, the liquid in the tube 470 and collector portion 60 will drain into the storage bottle 23 as the user removes the upper reservoir 21 and collar 24 from the storage bottle 23. Referring to FIG. 9, it is noted that the flow diverter may be accomplished by an extension of the outlet chute so that it guides liquid down to the bottom of the storage bottle.

The outlet end of the extension tube 472 is close to the bottom of the storage bottle so that the storage bottle is filled from at or near the bottom of the storage bottle to avoid splashing.

Figure 11A:
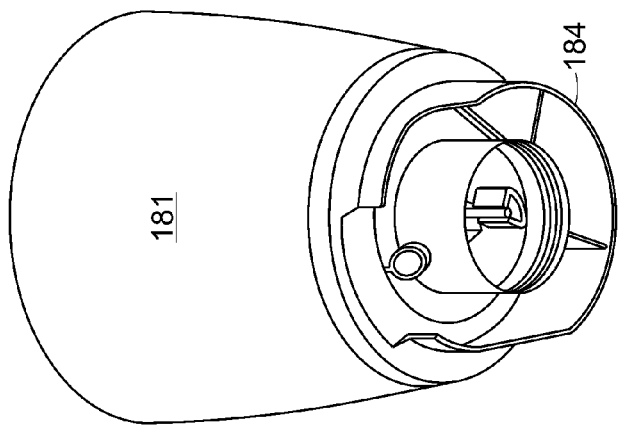
FIG. 11A-C shows an embodiment in which the sample reservoir and the vacuum collar are a single integral structure.
Figure 11B:
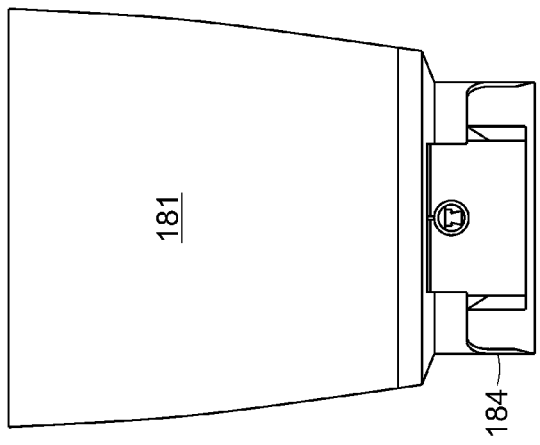
Figure 11C:
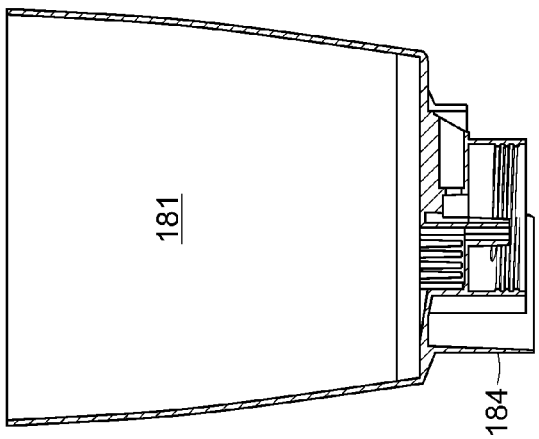

FIG. 11A-C shows an alternative embodiment in which a sample reservoir 181 and a vacuum collar 184 are a single integral structure. In other embodiments, other structures may be unified together into similar common compound structures. For example, the vacuum collar and the storage bottle may form a single common structure.

As shown in FIGS. 13 and 14, an embodiment of the present invention may include registration features 81 and 82 for orienting an inserted filter assembly 20 in a single fixed radial direction. As shown in FIG. 13A, the filter assembly 20 may include a loading channel 71 having within it a set of registration features 81. The base 28 would include a cradle 85 having corresponding registration features 82. The filter assembly 20 is docked on the base 28 by lowering the loading channel 72 over the cradle 85, FIG. 13B. The collar 24 has an open area that fits over the support arm 29 and facilitates aligning the registration features 81 and 82. The collar 24 guides the filter assembly 20 onto the cradle 85 until the registration features mate, FIG. 13C. Once in place, the vacuum outlet port 84 is automatically aligned with and sealed against a mating port 96 on the vacuum collar 24 so that the vacuum provided through the fluid conduit in the base is in communication with the liquid filter assembly 20. An O-ring or similar annular gasket on the vacuum outlet port 84 effectively seals the mated vacuum ports. The ports are beveled so that the weight of the filter assembly urges the ports together to form a more effective seal. This process can quickly and easily be performed one handed to provide convenient "load and go" functionality.

Although various exemplary embodiments of the invention have been disclosed, it should be apparent to those skilled in the art that various changes and modifications can be made without departing from the spirit and scope of the invention. It is intended that such changes and modifications be covered by the following claims.

What is claimed is:

1. A liquid filtering system comprising:
   an upper sample reservoir for receiving a volume of sample liquid;
   a sample filter positioned proximate a bottom of the sample reservoir for mechanically filtering the sample liquid;
   a lower storage bottle for receiving filtered sample liquid from the sample reservoir;
   a vacuum in fluid communication with the lower storage bottle to draw sample liquid through the sample filter into the storage bottle; and
   a flow diverter positioned to receive sample liquid drawn through the sample filter and to direct the sample liquid onto a sidewall of the lower storage bottle, wherein the flow diverter includes a bendable neck element in the upper portion of the lower storage bottle.

2. A liquid filtering system according to claim 1, further comprising a vacuum collar disposed between the upper sample reservoir and the lower storage bottle for applying the vacuum to the lower storage bottle and wherein the flow diverter is integral with the vacuum collar.

3. A liquid filtering system according to claim 1, wherein the flow diverter is integral with the lower storage bottle.

4. A liquid filtering system according to claim 1, wherein the upper sample reservoir and the lower storage bottle are aligned so as to tilt at a non-vertical angle.

5. A vacuum collar for use on a filtrate storage bottle for a liquid filtering system comprising:
   a vacuum port for connection to vacuum;
   a vacuum collar coupling structure for making connection to the storage bottle so that the vacuum is applied to the interior volume of the storage bottle; and a flow diverter having a surface that catches sample liquid drawn by the vacuum into the storage bottle and directs the sample liquid onto a sidewall of the lower storage bottle.

6. A vacuum collar according to claim 5, wherein the flow diverter includes a bendable neck element.

7. A vacuum collar for use on a filtrate storage bottle for a liquid filtering system comprising:
a vacuum port for connection to vacuum;
a vacuum collar coupling structure for making connection to the storage bottle so that the vacuum is applied to the interior volume of the storage bottle; and
a flow diverter tube connected to receive sample liquid drawn by the vacuum into the storage bottle and having an outlet end close to a bottom of the storage bottle so that sample liquid is guided down through the tube and out into the bottle near the bottom of the storage bottle.

8. A base for use with a liquid filter assembly comprising:
a weighted bottom to avoid tipping over;
a vacuum inlet port;
a support arm secured to the weighted bottom and having a vacuum outlet port arranged in a cradle for connection to the liquid filter assembly;
a fluid conduit connected between the vacuum inlet port and the vacuum outlet port; and
wherein the cradle is movable relative to the weighted bottom so as to hold the liquid filter assembly tilted at a non-vertical angle.

9. A base according to claim 8, wherein the support arm has flexibility to permit adjustment of the angle of the liquid filter assembly.

10. A base according to claim 8, wherein the cradle is pivotable with respect to the support arm to permit adjustment of the angle of the liquid filter assembly.

11. A liquid filtering system comprising:
at least one filter assembly including:
an upper sample reservoir for receiving a volume of sample liquid;
a sample filter positioned proximate a bottom of the sample reservoir for mechanically filtering the sample liquid;
a lower storage bottle for receiving filtered sample liquid from the sample reservoir;
a vacuum in fluid communication with the lower storage bottle to draw sample liquid through the sample filter into the storage bottle; and
a base for receiving a filter assembly to stably support the assembly in an adjustable orientation relative to vertical so that the filter assembly may be held in a tilted non-vertical orientation.

12. A liquid filtering system according to claim 11, wherein the vacuum is provided through the base and further comprising a vacuum collar disposed between the upper sample reservoir and the lower storage bottle for applying the vacuum from the base to the lower storage bottle.

13. A liquid filtering system according to claim 12, further comprising:
a vacuum controller on the base for regulating the vacuum.

14. A liquid filtering system according to claim 12, further comprising a vacuum controller directly connected by a hose to the base.

15. A liquid filtering system according to claim 11, wherein the base is weighted to avoid tipping over.

16. A liquid filtering system comprising:
at least one filter assembly including:
an upper sample reservoir for receiving a volume of sample liquid,
a sample filter positioned proximate a bottom of the sample reservoir for mechanically filtering the sample liquid;
a lower storage bottle for receiving filtered sample liquid from the sample reservoir; and
a vacuum in fluid communication with the lower storage bottle to draw sample liquid through the sample filter into the storage bottle;
a base for sitting on a work surface and for receiving a filter assembly to stably support the assembly;
a vacuum controller accessible atop the work surface for regulating the vacuum, and
a vacuum collar disposed between the upper sample reservoir and the lower storage bottle for applying the vacuum from the base to the lower storage bottle, wherein the vacuum is provided through the base.

17. A liquid filtering system according to claim 16, wherein the vacuum controller is on the base.

18. A liquid filtering system according to claim 17, wherein the vacuum controller includes a knob on the base having an OFF position for venting the fluid conduit to atmosphere so that no vacuum pressure is provided to the lower storage bottle.

19. A liquid filtering system according to claim 16, wherein the vacuum controller is attached onto a hose connected to the base.

20. A method for filtering liquid samples comprising:
securing a filter assembly above a work surface, the filter assembly including an upper reservoir above a filter and a storage bottle below the filter for receiving filtered liquid drawn through the filter;
depositing a liquid sample into the upper reservoir;
tilting the filter assembly to cause the filtered liquid sample to flow along a sidewall of the storage bottle;
applying a vacuum underneath the filter to draw liquid through the filter; and
adjusting a controller to regulate the applied vacuum to reduce foaming of the filtered liquid sample.

21. A method according to claim 20, further comprising directing flow of filtered liquid sample along a diverter onto a sidewall of the storage bottle.

22. A method according to claim 20, further comprising guiding filtered liquid sample through a tube and out into the storage bottle proximate a bottom of the storage bottle.

23. A liquid filtering system comprising:
an upper sample reservoir for receiving a volume of sample liquid;
a sample filter positioned proximate a bottom of the sample reservoir for mechanically filtering the sample liquid;
a lower storage bottle for receiving filtered sample liquid from the sample reservoir;
a vacuum in fluid communication with the lower storage bottle to draw sample liquid through the sample filter into the storage bottle;
a flow diverter positioned to receive sample liquid drawn through the sample filter and to direct the sample liquid onto a sidewall of the lower storage bottle; and
a vacuum collar disposed between the upper sample reservoir and the lower storage bottle for applying the vacuum to the lower storage bottle and wherein the flow diverter is integral with the vacuum collar.

24. A liquid filtering system according to claim 23, wherein the flow diverter includes a bendable neck element in the upper portion of the lower storage bottle.

25. A liquid filtering system according to claim 23, wherein the upper sample reservoir and the lower storage bottle are aligned so as to tilt at a non-vertical angle.

* * * * *